United States Patent [19]  
Braun et al.

[11] Patent Number: 4,790,306  
[45] Date of Patent: Dec. 13, 1988

[54] RESPIRATORY MASK HAVING A RIGID OR SEMI-RIGID, INSERT-MOLDED FILTRATION ELEMENT AND METHOD OF MAKING

[75] Inventors: David L. Braun, Lake Elmo; Donald L. Melvin, Maplewood, both of Minn.

[73] Assignee: Minnesota Mining and Manufacturing Company, St. Paul, Minn.

[21] Appl. No.: 100,830

[22] Filed: Sep. 25, 1987

[51] Int. Cl.$^4$ ............................................. A62B 23/02
[52] U.S. Cl. .................................. 128/206.12; 55/490; 264/274
[58] Field of Search .................... 55/490; 128/206.12, 128/206.17; 264/274

[56] References Cited  
U.S. PATENT DOCUMENTS  
3,861,381 1/1975 Witman et al. .................. 128/206.12

Primary Examiner—Gerald A. Michalsky  
Attorney, Agent, or Firm—Donald M. Sell; Roger R. Tamte

[57] ABSTRACT

A filtering device is made by inserting into an injection mold a porous, rigid or semi-rigid filtration element that has inflow and outflow faces separated by a peripheral surface and then injecting resin into the flow channel of the mold at a pressure and temperature such that the resin does not significantly penetrate into the peripheral surface beyond its surface pores. The resin can be a thermoplastic rubber and can form the facepiece of the resirator mask. An inhalation plenum for the mask can be formed at the same time by inserting into the flow channel of the mold a thin layer of a second resin which substantially does not melt at the pressure and temperature at which the first resin is injected. A complete respirator mask can be produced at a single station in a single insert-molding operation by inserting an exhalation valve and harness attachments together with said filtration element before injecting the first resin. Hence, the respiratory mask can be manufactured inexpensively while affording extraordinarily long service life.

21 Claims, 2 Drawing Sheets

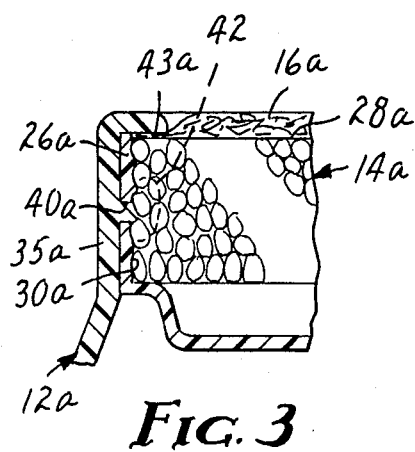
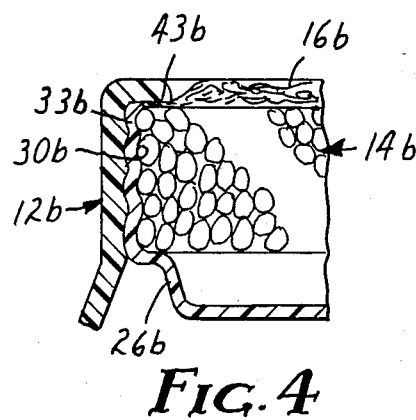
FIG. 3
FIG. 4
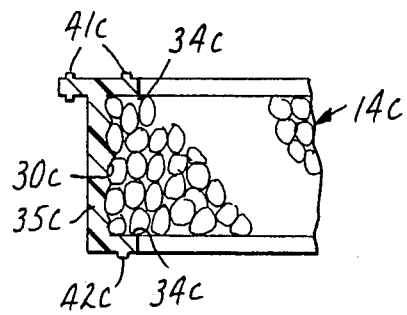
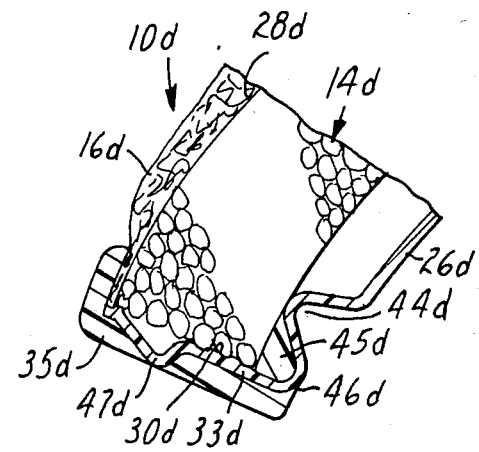
FIG. 5
FIG. 6
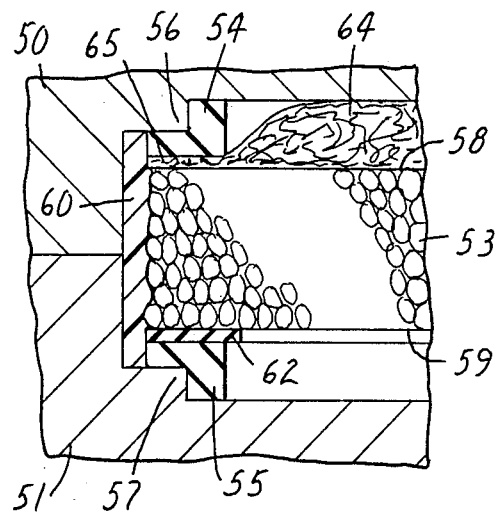
FIG. 7

RESPIRATORY MASK HAVING A RIGID OR SEMI-RIGID, INSERT-MOLDED FILTRATION ELEMENT AND METHOD OF MAKING

BACKGROUND OF THE INVENTION

1. Field of the Invention

The invention relates to mounts for filtration elements such as a mount provided by the facepiece of a respiratory mask. The invention specifically concerns a respiratory mask having a porous, rigid or semi-rigid filtration element or elements for protecting the wearer against hazardous gases and vapors. The invention also concerns a method of making a filtering device using an injection mold adapted to receive as an insert a porous, rigid or semi-rigid filtration element. By "semi-rigid" is meant that the filtration element is shape-retaining and can be moderately flexed by one's fingers.

2. Description of the Related Art

A respirator mask should have a soft, supple facepiece to permit the mask to be worn for prolonged periods without undue discomfort. When the respirator mask employs replaceable filters, the filter typically consists of a filtration element mounted in a casing which is threadably received into a complementary casing of the facepiece. Hence, there is the possibility of leakage between the filtration element and its casing, between the two casings, and between the complementary casing and the facepiece. Especially worrisome is the possibility of leakage between the two casings, because some users may be careless when replacing filters. Another problem with prior respiratory masks is that the filters often project from the facepiece to a degree interfering with the user's actions as well as with the user's vision. Such a respirator mask is shown in Maryyanek et al., U.S. Pat. No. 4,592,350.

After discussing problems with respirator masks of the replaceable filter type, Witman et al. U.S. Pat. No. 3,861,381 describes injection molding the shell or facepiece of a respirator mask which protects the wearer against particulate matter. The shell material is made to flow around individual fibers of a flexible, fibrous filtration element to provide a mechanical joining of the shell and filter. "The mold which shapes the shell and holds the filter during molding is provided with compression areas which pinch off the major portion of the filter while allowing the material of the shell to penetrate a predetermined distance into the filter thereby encapsulating and sealing the edges of the filter and joining it to the shell. Support pins may be used in the mold to locate the filter prior to the molding operation" (col. 2, lines 32-39). A "continuous circumferential portion of the filter in the vicinity of its periphery is compressed as at 14, to the point where it is no longer porous to the melted plastic, thus preventing the penetration of shell material into the working area of the filter during the molding operation" (col. 3, lines 44-51). The melted plastic flows into the interstices between the uncompressed fibers outside the line of compression and solidifies around those fibers while either melting those fibers or otherwise becoming bonded to the periphery of the filtration element.

The respirator mask illustrated in the Witman patent should be far less expensive to make than are respirator masks that have replaceable filters in that the respirator mask is assembled as the facepiece is formed.

A method of making a facepiece of a respiratory mask that is similar to that of the Witman patent is described in Bradley et al. U.S. Pat. No. 2,922,417. Like Witman, Bradley does not suggest the use of injection molding until after the edges of the filtration element have been sealed. In the Bradley patent, the sealing can be done by spraying adhesive onto the uncompressed edges of the filtration element while a continuous circumferential portion of the filter in the vicinity of its periphery is compressed to the point where it is not porous to the adhesive.

Boylan U.S. Pat. No. 3,183,285 concerns another method for creating a mount or gasket for a filtration element. After pouring an expandable plastic compound into a peripheral channel of a mold, the edges of the filtration element are moved into contact with the plastic compound. The upper mold member is closed and clamped, both closing the channel and pinching the filtration element along the line just inside the periphery of the filtration element. Then the plastic compound is allowed to expand to the limits of the closed channel, thus impregnating that portion of the filtration element that extends into the channel. Holloway et al. U.S. Pat. No. 3,235,633 concerns a method similar to that of the Boylan patent except that nothing is said about closing the mold into which the expandable plastic is poured.

3. Other Prior Art

Preferred semi-rigid filtration elements for use in the respiratory mask of the present invention are bonded absorbent granules as disclosed in Braun et al. European Patent Application No. EP-218348A (published April 15, 1987), which disclosure is here incorporated by reference. The filtration elements provide protection against gas and vapors and can also provide protection against particulate matter.

U.S. Pat. No. 4,664,683 (Degan et al.) also describes filtration elements useful in the respiratory mask of this invention.

SUMMARY OF THE INVENTION

The invention provides a respiratory mask which should offer advantages of the Witman patent while being more versatile and giving much longer service life. For example, the respiratory mask of the invention can be used to provide protection against hazardous gases and vapors in addition to filtering out particulate matter. The filtration element or elements are integrated into the facepiece, thus reducing danger of leakage and eliminating mounting hardware and its cost. By being integrated into the facepiece, the filtration element or elements can lie within or close to the profile the facepiece, thus both enlarging the wearer's field of vision and improving the wearer's mobility in constricted spaces. By integrating the filtration element or elements with the facepiece, the center of gravity can be back from the tip of the nose of an upright wearer toward the cheek area, thus reducing the tendency of the mask to bow the wearer's head. This makes the novel respiratory mask feel lighter to wear than does a respiratory mask of equal weight which has projecting filter cartridges and thus has a center of gravity further from the wearer's head.

Briefly, the novel respiratory mask differs from those of the prior art by having (1) a porous, rigid or semi-rigid filtration element which protects against hazardous gases and vapors and has broad inflow and outflow faces separated by a peripheral surface and (2) a facepiece comprising resilient, conformable resin which serves as a mount for the filtration element and seals its peripheral surface without significantly penetrating beyond the surface pores of the filtration element. The resin mount can seal directly to the peripheral surface of the filtration element, or the resin mount can include a barrier layer interposed between the facepiece and said peripheral surface. The barrier layer preferably is a thermoplastic resin which can be relatively thin and rigid and in a preferred embodiment of the invention, forms an inhalation plenum. The barrier layer may or may not conform and seal to said peripheral surface. If it does not conform thereto, either the barrier layer should be perforated or the resin mount should envelop at least one edge of the barrier layer and seal to the filtration element at the edge of the barrier layer, e.g., it may seal to the peripheral surface of the inflow face of the filtration element.

More broadly, the invention concerns any filtering device that includes a porous, rigid or semi-rigid filtration element which protects against hazardous gases and vapors and has inflow and outflow faces separated by a peripheral surface at which the filtration element is supported by a resin mount that seals the peripheral surface, as long as the resin does not significantly penetrate beyond the surface pores of the filtration element. For example, the mount of a novel filtering device can be shaped to fit into a filter-receiving socket of a respiratory mask that employs removable filters. Whether or not the novel filtering device is a respiratory mask, it can employ any filtration element disclosed in the above-cited European Patent Appln. No. EP-218348A and U.S. Pat. No. 4,664,883. Other filtration elements having similar physical characteristics can also be used.

The respiratory mask or other filtering device of the invention can be made using an injection mold adapted to receive as an insert a resilient, porous, rigid or semi-rigid filtration element that protects against hazardous gases and vapors and is formed to have inflow and outflow faces separated by a peripheral surface. Resin injected into the mold forms a mount for the rigid or semi-rigid filtration element, which resin mount may be the facepiece of a respiratory mask. Regardless of the form of the mount, the mold is so shaped that, upon being closed, it slightly compresses the filtration element to seal off the aforementioned inflow and outflow faces from the flow channel of the mold without collapsing the pores except to a minor extent at the edges of the those faces.

Briefly, the steps for making the novel respirator mask or other filtering device involve:
(1) inserting at least one filtration element into the mold,
(2) closing the mold,
(3) injecting resin into the flow channel of the mold at a pressure and temperature such that the resin does not significantly penetrate beyond the surface pores of said peripheral surface of the filtration element, and
(4) removing from the mold a filtering device, the filtration element of which is supported by a resin mount which seals its peripheral surface without significantly penetrating beyond the surface pores of the filtration element.

The filtration element can be centered by conventional means such as tooling slides, preferably acting at the peripheral surface of the filtration element.

In step (1), there can also be inserted into the mold a thin piece of resin which separates said peripheral surface from the flow channel of the mold and thus acts as a barrier layer between the filtration element and the injected resin which acts as a sealing layer. When the barrier layer is softened by the heat of the injected resin, it may conform to and seal the peripheral surface even though it substantially is not caused to extend into pores of the filtration element at the pressure and temperature applied in step (3). An extension of the barrier layer can be shaped to form an inhalation plenum for a respirator mask.

It thus is possible to form a respirator mask at a single station in an insert-molding operation, because the resin injected in step (3) can form the facepiece which seals to said filtration element. By inserting in step (1) an exhalation valve and harness attachments into the flow channel of the mold together with said filtration element, the filtering device obtained in step (4) can immediately be put to use as a respirator mask.

It is surprising that it is possible to control the pressure and temperature of molding so that the injected resin only penetrates a short distance into the filtration element. In prototype filtering devices that have been made to date without a barrier layer, the injected resin typically penetrates from 0.2 to 2 mm into the filtration element. It also is surprising that an adequate shutoff can be obtained by slightly compressing the filtration element in the injection mold without collapsing the surface pores except to a limited extent where the filtration element is compressed. To date, a variety of filtering devices of the invention have been created without any flash being formed through the shutoffs between the injection mold and the filtration element.

When a foamed resin is used to form the resin mount, the filtration element can have a compressive modulus as low as 2 bars/cm as measured by ASTM Test Designation D695-85 using a sample 2.54 cm by 2.54 cm by 1.9 cm and compressing either square face at a rate of 0.635 cm/min. Because unfoamed resins require higher injection pressures, the filtration element should have a higher compressive modulus, e.g., above 25 bars/cm when the resin mount is of relatively simple geometry. For resin mounts of more complex shape such as facepieces, the compressive modulus should be at least 50 bars/cm measured between 5 to 10 percent deflections of the sample face.

The resin mount of the novel filtering device can be virtually any thermoplastic or thermoset resin. When the resin mount forms the facepiece of a respiratory mask, the facepiece preferably is formed from a thermoplastic rubber which permits short molding cycles. Preferred thermoplastic rubbers include plasticizer, e.g., oil-modified block copolymers. Plasticizers make the facepiece more comfortable to wear and offer other advantages, e.g., (1) reduce the viscosity of the injected resin and thus make it easier to fill the mold at a given pressure, and (2) reduce the raw material cost. However, when the plasticized resin is in direct contact with the filtering element, the plasticizer can migrate into the filtering element, thus reducing its efficiency. Hence, when using a plasticized resin to form the resin mount of the novel filtering device, a barrier layer (as described hereinabove) preferably is interposed between the plasticized resin and the filtration element, and the barrier layer preferably is free from perforations.

A barrier layer provides additional advantages, e.g., by forming it with registration bumps, it can keep the filtration element centered during the injection molding process. Also, extensions of the barrier layer can serve as attachment tabs for straps and as a plenum of a respiratory mask. Whether or not a resin mount of the invention includes a facepiece of a respiratory mask, a barrier layer permits the injected resin to form a soft, conformable sealing layer while the relatively rigid barrier layer provides means for securing the resin mount.

Preferred barrier layer materials include polyolefins, preferably polypropylene. When the sealing layer of the resin mount is a block copolymer, at least one block is preferably chemically similar to the barrier layer. It may be desirable to blend into the injected resin a small amount, e.g., 5%, of the barrier layer material to facilitate bonding between the barrier and sealing layers of the resin mount.

THE DRAWING

The invention may be more understandable by reference to the drawing, all figures of which are schematic, wherein.

Each of FIGS. 3-6 is a fragmentary cross section through a filtering device of the invention including a mount for a porous, substantially rigid filtration element that protects against hazardous gases and vapors; and FIG. 7 is a fragmentary cross section through a tool being used for injection molding of a filtering device of the invention.

Figure 1:
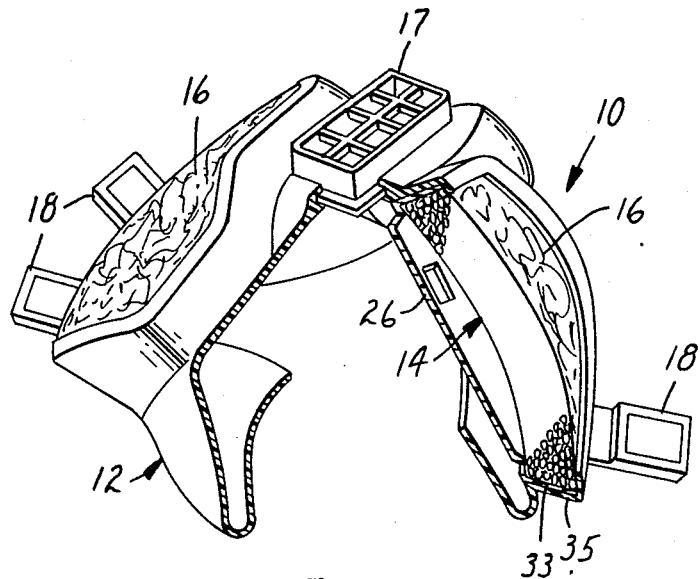
FIG. 1 is a perspective view, partly cut away, of a respiratory mask of the invention.

The respiratory mask 10 shown in FIG. 1 has a facepiece 12 that serves as a mount for a pair of porous, semi-rigid filtration elements 14 made of bonded absorbent granules to provide protection against hazardous gases and vapors. Covering each of the filtration elements is a fibrous layer 16 which acts as a prefilter to remove particulate matter. The facepiece 12 also serves as a mount for an exhalation valve 17 and is fitted with harness attachments 18.

Figure 2:
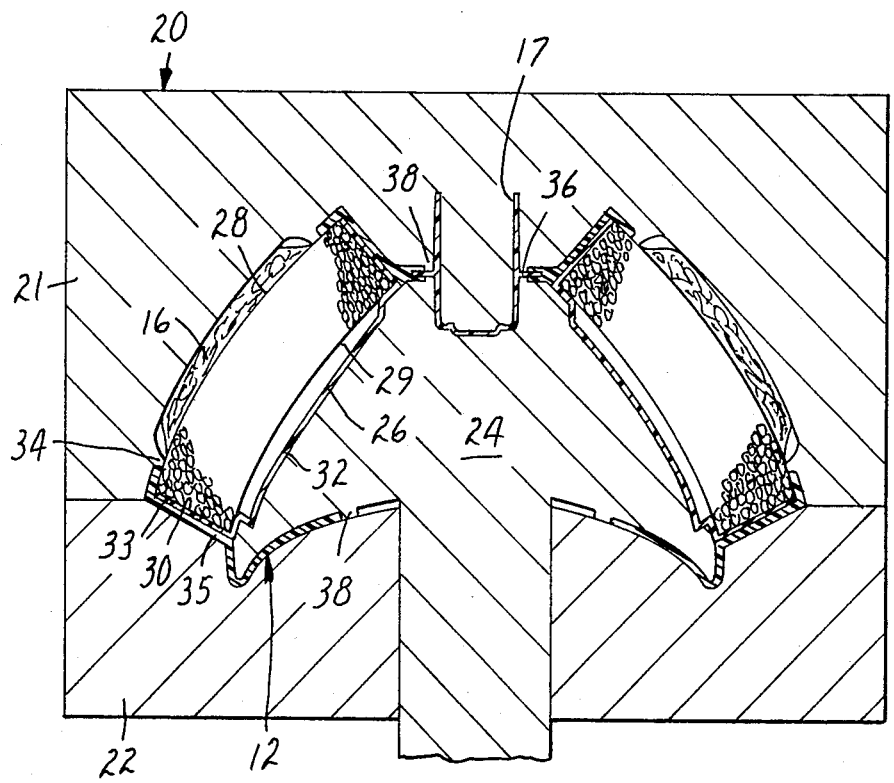
FIG. 2 is a cross section through an injection mold being used to form the respiratory mask of FIG. 1.

Referring to FIG. 2, the respiratory mask 10 can be produced at a single station in an insert-molding operation using an injection mold 20 which includes a cavity block 21, a force block 22, and a core 24. The injection mold 20 is adapted to receive as inserts two resilient, porous, semi-rigid filtration elements 14, two fibrous layers 16, two thin pieces 26 of a thermoplastic resin, an exhalation valve 17, and harness attachments 18 (not shown in FIG. 2). Each of the filtration elements 14 has a broad inflow face 28 and a broad outflow face 29 separated by a continuous peripheral surface 30. Before being inserted, each of the thermoplastic pieces 26 had been preformed into the shape of an inhalation plenum 32 terminating in a barrier layer 33 that rests against the peripheral surface 30 of one of the filtration elements 14 when the plastic pieces and filtration elements are inserted into the injection mold 20.

After positioning the inserts, the mold 20 is closed as shown in FIG. 2. A shut-off ridge 34 partially compresses the filtration element 14 to seal off the broad faces from the flow channel of the mold without collapsing the pores at the peripheral surfaces 30. A resin, preferably a thermoplastic rubber, is injected to form the facepiece 12 including a pair of resin mounts 35, each of which extends completely around one of the barrier layers 33 of the thermoplastic pieces 26. The heat of the injected resin softens the barrier layers 33, and the injection pressure forces each of those barrier layers to conform to and seal the peripheral surface 30 without penetrating the pores of the filtration element 14 at that surface. Where the injected resin contacts the fibers of the fibrous layer 16, it melt-bonds to and softens the fibers, and the softened fibers conform to the peripheries of the inflow faces 28 of the filtration elements 14, thus enhancing the seal. The injected resin also flows around flanges 36 of the exhalation valve 17 to complete a seal and fills the flow channel of the mold 20 between shut-offs 38.

When the mold is opened, the respiratory mask 10 that has been formed is ejected and is ready for immediate use by merely attaching straps to the harness attachments 18.

Each of FIGS. 3, 4 and 6 shows a fragment of a respiratory mask which is identical to that of FIG. 1 except for the manner in which its semi-rigid filtration elements are supported. In FIG. 3, the injected resin forming a facepiece 12a (including a resin mount 35a) has flowed through a small perforation 40a in a thin piece 26a of thermoplastic resin and penetrated at 42 into surface pores of the peripheral surface 30a of the filtration element 14a near the perforation 40a to reinforce the mount. Before being inserted into the mold, fibers of the fibrous layer 16a had been compressed with heat to near-film density to form a barrier layer 43a between the injected resin and the periphery of the edges of the inflow face 28a of the filtration element 14a.

In FIG. 4, the heat of the injected resin forming a facepiece 12b has sealed to and softened a thin piece 26b of thermoplastic resin, and the pressure of the injected resin has forced the softened piece 26b to conform to the peripheral surface 30b of a filtration element 14b, thereby forming a barrier layer 33b between the facepiece 12b and the filtration element 14b. The fibers of the fibrous layer 16b had been compressed to form a second barrier layer between the facepiece 12b and the filtration element 14b.

FIG. 5 shows a fragment of a filtering device including a resin mount 35c for a semi-rigid filtration element 14c that could be used in a powered-air purifier or could fit into a filter-receiving socket of a respiratory mask. The resin mount 35c has been formed in a mold (not shown) in a manner similar to that used in FIG. 2. That is, while the filtration element 14c has been partially compressed at 34c by shut-offs (not shown), a thermoplastic resin has been injected to form a resin mount 35c and, in doing so, has penetrated into surface pores of the peripheral surface 30c of the filtration element 14c, thus providing both a strong support and a seal. The resin mount 35c includes two pairs of opposed sealing ridges 41c and 42c to facilitate coupling to a filter-receiving socket.

In FIG. 6, a respiratory mask 10d employs filtration elements 14d, each having a curved shape to follow the face of a wearer. A fibrous layer 16d covers each inflow face of the filtration elements 14d. Because of this curved shape and the acute angle between the peripheral surface 30d of each filtration element 14d and the tangent to the inflow face 28d, the force block of the tool (not shown) in which the mask was formed was provided with a boss at 44d. A thin piece 26d of thermoplastic resin provides a barrier layer 33d which has been formed with registration bumps (one of which 47d is shown) as well as a concavity which has been filled by silicone rubber to provide a boss 45d that mates with the aforementioned boss 44d on the tool, thus counteracting the hydraulic pressure of the injected synthetic resin 35d. This stabilizes the shut-off at 46d and ensures against a flash that otherwise might form.

In FIG. 7, an injection mold has a pair of symmetrical molding cavities 50 and 51 adapted to receive a cylindrical filtration element 53 and a pair of silicone rubber rings 54 and 55, each formed with a notch that mates with shoulders 56 and 57 of the molding cavities 50 and 51, respectively. When the mold is closed, the silicone rubber rings are compressed against the inflow and outflow faces of the filtration element to provide shut-offs to prevent flash from flowing onto the inflow and outflow faces 58 and 59 of the filtration element 53 when a thermoplastic resin is injected to form a resin mount 60. The injected resin penetrates into surface pores of the peripheral surface of the filtration element 53. An annular rubber gasket 62 is positioned between the outflow face 59 and the corresponding rubber ring 55. Covering the inflow face 58 is fibrous layer 64, fibers of which have been compressed to form a barrier layer 65.

In an early experiment, an injection mold was made as illustrated in FIG. 7 except omitting the shoulders 56 and 57 and using unnotched silicone rubber rings. The injected melt flashed by the outer peripheral edges of the silicone rubber rings.

In the following examples, all parts are by weight.

EXAMPLE 1

Porous semi-rigid filtration elements were prepared in 73 mm diameter cylindrical form by blending 80 parts of activated carbon (Witco No. 950 passing 1000 $\mu$m openings and held by 420 $\mu$m openings) with 20 parts of thermoplastic polyurethane ("Quinn" P3429 passing 149 $\mu$m openings and held by 105 $\mu$m openings) and heating the blend to 200° C. followed by compressing it to a predetermined thickness with a piston. The resultant thicknesses were as shown in Table A.

An injection molding tool as shown in FIG. 7 was sized to receive one of the cylindrical filtration elements while leaving an annular gap around the peripheral surface into which resin could be injected. The silicone rubber rings 54 and 55 had 45–50 Shore A durometer. The injected resin was a plasticized thermoplastic rubber, namely, an oil-modified styrene-ethylene/butylene-styrene block copolymer ("Kraton" G7705 from Shell Chemical Co.). The injection molding tool was mounted in a horizontal reciprocating-screw injection molding machine (75-ton Van Dorn Model 75-RS-3F equipped with a standard screw) using temperatures of 188° C. (rear), 215° C. (middle), and 221° C. (front). Molding conditions are reported in Table A. A 30 second cool-down time was used.

TABLE A

| Run No. | Filtration Element Thickness (mm) | Injection Time/Boost Time (sec) | Injection Pressure/ Boost Pressure (Bars) |
|---|---|---|---|
| A | 19.3 | 4/3 | 483/345 |
| B | 19.5 | 4/3 | 483/345 |
| C | 19.4 | 4/3 | 483/345 |

In Run A, the filtration element was the only insert. In Run B, a fibrous layer (like layer 64 of FIG. 7) covered both the inflow and outflow faces of the filtration element. The fibrous layers comprised nonwoven polyester web. In Run C, a sheet of rubber 0.63 mm thick covered each of the inflow and outflow faces of the filtration element and upon being cut open would provide gaskets similar to the gasket 62 of FIG. 7.

In the filtering device obtained in each of Runs A, B and C, the injected synthetic resin fully sealed the peripheral surface of the filtration element and provided a mount for the filtration element, which mount had raised seal surfaces at the edges of the inflow and outflow faces. There was no flash in any of Runs A, B or C.

In Run B, the injected resin bonded to fibers at the peripheries of the fibrous layers. One of the fibrous layers maintained registry with the filtration element and was sealed around its entire periphery, whereas the other fibrous layer had moved slightly out of registry. To avoid this problem, the edges of each of the fibrous layers preferably are tacked to the filtration element before they are inserted into the mold.

In Run C, one of the rubber sheets maintained good registry while the other moved slightly out of registry. To avoid this problem, the rubber sheet could be formed with a lip or other mechanical feature that mates with a feature of either the filtration element or the mold.

EXAMPLE 2

Porous semi-rigid filtration elements were prepared in the curved geometry of FIG. 6 by the method of Example 1 except that "Cenapro" carbon was used instead of the "Witco" carbon and the mold was shaped to provide for the curvature. A continuous peripheral boss (as at 44d in FIG. 6) was provided on the tool, and a mating boss (boss 45d of FIG. 6) was provided by smearing an air-curable silicone rubber into the concavity of a thin, rigid piece of thermoplastic resin that would form the plenum 26d of FIG. 6. The mating bosses counteracted the force of the injected synthetic resin. The periphery of the fibrous layer 16d had been adhesively tacked to the filtration element 14d and was stabilized by contact posts (not shown in FIG. 6) bearing against about 50% of its area. A V-shaped metal ridge was sized to imprint the fibrous layer 16d and filtration element 14d to a depth of about 0.6 mm, thus acting as a shut-off.

The injection molding tool was mounted in a vertical reciprocating-screw injection-molding machine (100-ton Stokes Model 702-14 equipped with a standard screw). The injected resin was a plasticized thermoplastic rubber, namely, an oil-modified styrene-ethylene/-butylene-styrene block copolymer ("J-Von" 3000L-33A, available from J-Von, a division of Jones & Vinning, Inc., Leominster, MA). Molding conditions were (1) temperatures: nozzle 199° C., front 232° C., middle 232° C., (2) hold pressure 138 Bars, (3) injection speed 12.7 sec., (4) screw pullback 1.27 cm, (5) shot size 8.1 cm, (6) die close 30 sec. A series of four filtering devices were made in succession, and in all four the resulting resin mount was fully filled out with no flash. All inserted parts of each of the filtering devices maintained good registry and were effectively sealed.

COMPARATIVE EXAMPLE 2

When filtering devices were made as in Example 2, except that the tool boss and the plenum boss were not provided, there was flash on the lower shutoff.

EXAMPLE 3

Filtration elements similar to those of Example 2 were made using 85.2 parts "NACAR" G214D carbon (passes 1680 $\mu$m openings and held by 840 $\mu$m openings) blended with 14.8 parts "Quinn" PS 455-100 polyurethane (passes 297 $\mu$m openings and held by 44 $\mu$m openings) as a binder. Each filtration element was then combined with a sleeve over the peripheral surface made by vacuum forming 0.76 mm polypropylene film (Film #78P4-2, KORO Corp., Hudson, MA) directly onto the porous filtration element. A nonwoven fibrous layer of a stably charged, fibrillated polypropylene film (100 gr/m² "Filtrete" from 3M) was adhesively tacked to the edges of the inflow face of each filtration element.

Each assembly was then inserted into an injection molding tool and injected with a synthetic resin as specified in Table B to provide a filtering device. The resulting geometry was as is shown in FIG. 4 except that each of the facepieces 12b extended only slightly beyond the outflow face of the filtration element 14b, and thermloplastic piece 26b was trimmed to extend only 6.3 mm inward from the peripheral surface 30b. Molding conditions and identification of the injected resin are reported in Table B.

TABLE B

|  | Injected Synthetic Resin | | |
| --- | --- | --- | --- |
|  | J-Von[1] | Elastalloy[2] | Polypropylene[3] |
| Nozzle Temperature (°C.) | 215 | 210 | 260 |
| Front Temperature (°C.) | 210 | 204 | 260 |
| Middle Temperature (°C.) | 199 | 188 | 249 |
| Mold Temperature (°C.) | 24 | 24 | 65 |
| Injection Pressure (bars) | 86 | 86 | 15.5 |
| Hold Pressure (bars) | 86 | 86 | 16.2 |
| Injection Forward (sec) | 2.5 | 2.5 | 2.5 |
| Boost Time (sec) | 4.5 | 4.5 | 4.5 |
| Shot Size (ml) | 10.34 | 10.34 | 10.34 |
| Hydraulic Pressure (bars) | 103 | 103 | 103 |

[1]"J-Von" 3000L-33A described hereinabove
[2]"Elastalloy" #2134, G.L.S. Plastics, Woodstock, IL
[3]PP6523, Himont, Inc., Wilmington, DE Table C reports performance testing of the filtering devices of Example 3. The testing employed a carbon tetrachloride challenge according to NIOSH Standard 30 CFR Part II, Subpart L, Section 11.162-8, except that the flow was halved to 32 liters/min. to accommodate a single filter. Test conditions were concentration: 1000 ppm±10; humidity: 50%±2%; temp: 25° C.±2° C. Each result reported in Table C is an average of four tests.

TABLE C

| Average service life ± 1σ (minutes) after storage at 65° C. | | | |
| --- | --- | --- | --- |
|  | Storage Time in Weeks | | |
| Mount Resin | 0 | 4 | 8 |
| "J-Von" | 55 ± 3 | 56 ± 5 | 52 ± 7 |
| "Elastalloy" | 54 ± 4 | 53 ± 2 | 34 ± 12 |
| Polypropylene | 59 ± 2 | 58 ± 1 | 57 ± 2 |

The reduced service life of the filtering devices made with "Elastalloy" thermoplastic rubber may be due to migration of plasticizer from the rubber into the filtration element in the absence of a barrier layer.

EXAMPLE 4

A semi-circular channel of 6.35 mm cross sectional radius was milled into an aluminum plate in a circular pattern viewed from above. The inner and outer diameters of the channel were 92 and 118 mm respectively. A hemispherical dome-shaped filtration element was made of bonded absorbent granules consisting of 82% of the activated carbon of Example 1 and 18% of nylon powder adhesive (Polymer Corp. 1535 SGJ,) which had passed through 74 μm openings. Its outer diameter was 120 mm, and its thickness was 16 mm. The filtration element was held over the milled circulator channel using hand pressure.

A thermoplastic resin (Findley X998-337-01) was foamed to about 50% final void fraction using N₂ gas in a Nordson hot-melt foam machine, Model 101B. The foam was injected through a small access hole into the semi-circular channel bounded by the bonded filter edge. It was found that the solidified foam was successfully bonded to the annular edge of the filtration element, providing a satisfactory edge seal. Penetration into the edge pores of the filter was about 1–2 mm providing good mechanical anchoring. The solidified foam provided a resin mount for the filtration element.

EXAMPLE 5

A tool was cast from epoxy resin in the general configuration of FIG. 2 of the drawing except that it had no provision for an exhalation valve insert. The thickness of the flow channel in areas of the facepiece was about 5 mm.

Two filtration elements were made using 82 parts of carbon (Calgon BPL passing 1680 μm openings and held by 590 μm openings) and 18 parts of a thermoplastic polyurethane resin as used in Example 1. These were nested in vacuum-formed plenums, and the inflow face was covered with a fibrous layer as in Example 3.

The assemblies were loaded into the tool, and the tool was clamped with large C-clamps. The thermoplastic rubber of Example 4 was foamed using N₂ gas and injected (using a Nordson FM-151 hot-melt foam machine) into the flow channel of the tool through a small access hole between the filtration elements. Process conditions were: (1) hose temperature 138° C., 2) N₂ pressure 2.75 bars, (3) panel gas 0.27 bars, (4) pump speed 300 rpm, (5) tank temperature 138° C., (6) loop pressure 41.4 bars, (7) gas valve ¾ turn open. The resulting respirator mask had remarkable facial comfort because of the softness of the foam. Examination showed that the filtration elements, the fibrous layer, and the plenum had been formed into an integral structure having good seals and mechanical integrity.

EXAMPLE 6

An injection molding tool in the configuration of FIG. 2 was made using a powder-metalurgy process. The inflow face shut-off ridge 34 was configured to indent the filtration element by 0.7 mm to eliminate flash. The tool parting lines were matched using electric discharge machining. Ejector pins were incorporated into the force block 22 to bear against the barrier layers 33. The tool was mounted in the injection molding machine of Example 2.

The curved filtration elements 14 of FIG. 2 were made using 85 parts of carbon (CalChar GMS 70 passing 1680 μm openings and retained by 840 μm openings) and 15 parts of thermoplastic polyurethane of Example 3. Its compressive modulus was 67 bars/cm measured between 5 and 10% deflections (average of nine specimens). The fibrous layer 16 had two layers, the inner being stably charged polypropylene blown microfibers (basis weight 50 gr/m²), the outer being a fibrillated web as in Example 3. The edges of the two fibrous layers were thermally sealed to the outer 3 mm of the broad faces of the filtration elements. The plenums 32 were vacuum formed from the polypropylene film of Example 3, each with two strap-attachment tabs (not shown in FIG. 2). After nesting the filtration elements into the plenums, they were inserted into the tool.

The molding machine was set up using the following conditions: (1) mold temperature 65° C., (2) middle and front barrel temperature 193° F., (3) nozzle temperature 199° C., (4) injection pressure 88 bars,(5) hold pressure 62 bars, (6) boost pressure 68.9 bars, (7) back pressure 0.34 bars (8) injection speed of ram 12.7 cm/sec, (9) die close time 42 seconds, (10) hold time 8 seconds, (11) booster time 0 seconds, and (12) transfer from injection to hold at 1.16 seconds.

Using these conditions and the "J-Von" thermoplastic rubber of Example 3, a number of respirator masks were made, each having the attributes of the respirator mask of Example 5.

One of these was tested under a carbon tetrachloride challenge according to the NIOSH Test of Example 3 except that the full 64 liters/min. flow was used. The service life was 120 minutes compared to a NIOSH requirement of 50 minutes.

COMPARATIVE EXAMPLE 6

Attempts were made to make respirator masks in the same way as in Example 6 except using filtration elements having an average compression modulus of 38 bars/cm measured between 5 and 10% deflections. Flash occurred past the shut-off 34 and between the plenum 32 and the core 24 as seen in FIG. 2.

We claim:

1. Filtering device comprising a porous, rigid or semi-rigid filtration element which protects against hazardous gases and vapors and has inflow and outflow faces separated by a peripheral surface at which the filtration element is supported by a resin mount that seals the peripheral surface without significantly penetrating beyond the surface pores of the filtration element.

2. Filtering device as defined in claim 1 wherein said filtration element comprises bonded absorbent granules.

3. Filtering device as defined in claim 1 wherein said resin mount comprises thermoplastic rubber.

4. Filtering device as defined in claim 3 and having a barrier layer of thermoplastic resin between the thermoplastic rubber and the peripheral surface of the filtration element.

5. Filtering device comprising a porous, rigid or semi-rigid filtration element which protects against gases and vapors and has inflow and outflow faces separated by a peripheral surface at which the filtration element is supported by a resin mount comprising
   (1) a barrier layer which conforms to said peripheral surface but substantially does not penetrate said element, and
   (2) a sealing layer which is bonded to the barrier layer and does not contact the filtration element except at the perimeter of its inflow and outflow faces.

6. Filtering device as defined in claim 5 wherein the sealing layer comprises a resilient, conformable thermoplastic rubber, and the barrier layer comprises a relatively thin and rigid thermoplastic resin.

7. Filtering device as defined in claim 6 wherein an extension of the sealing layer forms the facepiece of a respiratory mask and an extension of the barrier layer forms a plenum.

8. Respirator mask comprising a porous, substantially rigid filtration element that has broad inflow and outflow faces separated by a peripheral surface and is supported by a facepiece comprising resilient, conformable resin which seals the peripheral surface without significantly penetrating beyond the surface pores of the filtration element.

9. Respirator mask as defined in claim 8 wherein the resin of said facepiece is foamed.

10. Respirator mask as defined in claim 8 wherein the resin of said facepiece is an oil-modified styrene-ethylene/butylene-styrene copolymer.

11. Respirator mask as defined in claim 10 and having a barrier layer of thermoplastic resin between the facepiece and said peripheral surface of the filtration element.

12. Respirator mask as defined in claim 11 wherein said barrier layer is formed with at least one perforation, and the resin of the facepiece extends through said perforation and into surface pores of the filtration element at its peripheral surface.

13. Respirator mask as defined in claim 11 wherein an extension of said barrier layer forms an inhalation plenum.

14. Method of making a filtering device using an injection mold adapted to receive as an insert a resilient, porous, substantially rigid filtration element that has inflow and outflow faces separated by a peripheral surface, the mold being formed so that, upon being closed, it partially compresses the filtration element at said peripheral surface to seal off said inflow and outflow faces from the flow channel of the mold, said method comprising the steps of:
   (1) inserting the filtration element into the flow channel of the mold,
   (2) closing the mold,
   (3) injecting resin into the flow channel of the mold at a pressure and temperature such that the resin does not significantly penetrate beyond the surface pores of said peripheral surface of the filtration element, and
   (4) removing from the mold a filtering device of which said filtration element is supported by a mount formed by said resin.

15. Method as defined in claim 14 wherein the mold is shaped so that said resin forms a facepiece of a respirator mask.

16. Method as defined in claim 15 wherein step (1) also involves inserting into the flow channel of the mold a thin piece of a thermoplastic resin that rests against said peripheral surface and provides a barrier layer between the injected resin and the filtration element.

17. Method as defined in claim 16 wherein said thin piece of thermoplastic resin is formed with an extension which forms the inhalation plenum of said respirator mask.

18. Method as defined in claim 17, step (1) of which further involves inserting into the mold an exhalation valve and harness attachments so that the filtering device obtained in step (4) can immediately be put to use as a respirator mask.

19. Filtering device made by the method of claim 14.

20. Method of making a filtering device using an injection mold adapted to receive as an insert a resilient, porous, substantially rigid filtration element that has inflow and outflow faces separated by a peripheral surface, the mold being formed so that, upon being closed, it partially compresses the filtration element at said peripheral surface to seal off said inflow and outflow faces from the flow channel of the mold, said method comprising the steps of:
   (1) inserting into the flow channel said filtration element and a piece of thermoplastic resin covering said peripheral surface of the filtration element,
   (2) closing the mold, (3) injecting resin into the flow channel at a pressure and temperature such that the piece of thermoplastic resin is softened and conforms to and seals the peripheral surface of the filtration element but substantially does not extend into its pores, and
(4) removing from the mold a filtering device of which said filtration element is supported by a mount formed by both said injected resin and said piece of thermoplastic resin.

21. Filtering device made by the method of claim 20.